(12) United States Patent
Perbost

(10) Patent No.: US 6,900,048 B2
(45) Date of Patent: May 31, 2005

(54) BIOPOLYMER ARRAYS AND THEIR FABRICATION

(75) Inventor: Michel G. M. Perbost, Cupertino, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 253 days.

(21) Appl. No.: 09/895,050

(22) Filed: Jun. 29, 2001

(65) Prior Publication Data

US 2001/0044115 A1 Nov. 22, 2001

Related U.S. Application Data

(62) Division of application No. 09/356,249, filed on Jul. 16, 1999.

(51) Int. Cl.[7] .............................................. C12M 1/54
(52) U.S. Cl. ..................................... 435/287.3; 422/100
(58) Field of Search ....................... 422/100; 435/287.1, 435/287.3, 6, 91.1; 427/333, 340, 385.5

(56) References Cited

U.S. PATENT DOCUMENTS

| | | | |
|---|---|---|---|
| 4,415,732 A | | 11/1983 | Caruthers et al. |
| 5,449,754 A | | 9/1995 | Nishioka |
| 5,700,919 A | | 12/1997 | Seliger et al. |
| 5,807,522 A | | 9/1998 | Brown et al. |
| 5,859,233 A | * | 1/1999 | Hirschbein et al. |
| 5,874,554 A | | 2/1999 | Gamble et al. |
| 5,902,878 A | | 5/1999 | Seliger et al. |
| 5,908,926 A | | 6/1999 | Pirrung et al. |
| 6,001,966 A | | 12/1999 | Pieken et al. |
| 6,184,347 B1 | | 2/2001 | Perbost et al. |
| 6,300,137 B1 | | 10/2001 | Earhart et al. |

FOREIGN PATENT DOCUMENTS

| | | | | |
|---|---|---|---|---|
| WO | WO 94/27719 | | 12/1994 | |
| WO | WO 95/25116 | * | 9/1995 | ............... 427/333 |
| WO | WO 97/19749 | | 6/1997 | |
| WO | WO 98/41531 | | 9/1998 | |
| WO | WO 00/13796 | | 3/2000 | |

OTHER PUBLICATIONS

Marshall, A., Hodgson, J., "DNA Chips: An Array of Possibilities", Nature Biotechnology, vol. 16, pp. 27–31, 1998.
Pirrung, M.C., "Spatially Addressable Combinatorial Libraries", Chem. Rev., vol. 97, pp. 473–488, 1997.
Pease et al., "Light-generated oligonucleotide arrays for rapid DNA sequence analysis", Proceedings of the National Academy of Sciences, USA, vol. 91, pp. 5022–5026, 1994.
U.S. Appl. No. 09/972,256, filed Oct. 5, 2001, Earhart et al., titled, "Method for Synthesizing a Specific, Surface-Bound Polymer Uniformaly over an Element of a Molecular Array".

* cited by examiner

Primary Examiner—W. Gary Jones
(74) Attorney, Agent, or Firm—Gordon Stewart

(57) ABSTRACT

A method of fabricating an addressable array of biopolymers on a substrate using a biomonomer with a first linking group which must be activated for linking to a substrate bound moiety, and apparatus and computer program products for executing the method. The method includes forming on a region of the substrate carrying the substrate bound moiety, a solid activator composition. A biomonomer containing fluid composition is deposited on the region so that the solid activator activates the first linking group and the biomonomer links to the substrate bound moiety. The foregoing steps may be repeated, wherein a biomonomer deposited and linked to the substrate bound moiety in one cycle is the substrate bound moiety for the next cycle, so as to form the biopolymer.

5 Claims, 3 Drawing Sheets

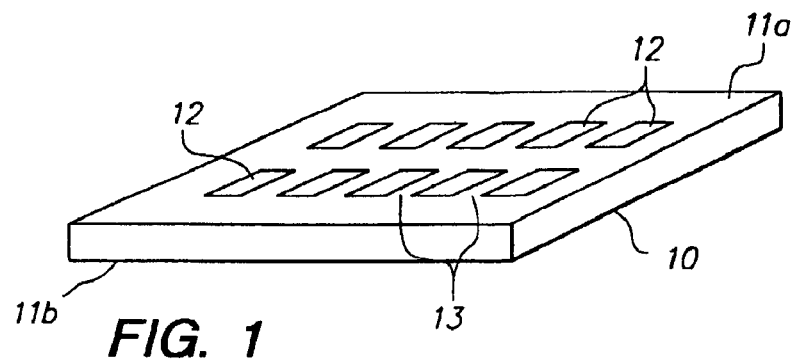
FIG. 1
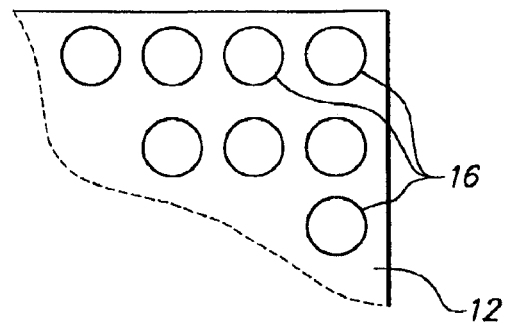
FIG. 2
FIG. 3

BIOPOLYMER ARRAYS AND THEIR FABRICATION

CROSS REFERENCE TO RELATED APPLICATION(S)

This a divisional of copending application Ser. No. 09/356,249 filed on Jul. 16, 1999.

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions (sometimes referenced as features or spots) of usually different sequence polynucleotides arranged in a predetermined configuration on a substrate. The arrays, when exposed to a sample, will exhibit a binding pattern. This binding pattern can be observed, for example, by labeling all polynucleotide targets (for example, DNA) in the sample with a suitable label (such as a fluorescent compound), and accurately observing the fluorescence pattern on the array. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated using either deposition of the previously obtained biopolymers or in situ synthesis methods. The deposition methods basically involve depositing biopolymers at predetermined locations on a substrate which are suitably activated such that the biopolymers can link thereto. Biopolymers of different sequence may be deposited at different regions of the substrate to yield the completed array. Typical procedures known in the art for deposition of previously obtained polynucleotides, particularly DNA such as whole oligomers or cDNA, are to load a small volume of DNA in solution in one or more drop dispensers such as the tip of a pin or in an open capillary and, touch the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed. Alternatively, the DNA can be loaded into a drop dispenser in the form of an inkjet head and fired onto the substrate. Such a technique has been described, for example, in PCT publications WO 95/25116 and WO 98/41531, and elsewhere.

The in situ synthesis methods include those described in U.S. Pat. No. 5,449,754 for synthesizing peptide arrays, as well as WO 98/41531 and the references cited therein for synthesizing polynucleotides (specifically, DNA) using phosphoramidite or other chemistry. Such in situ synthesis methods can be basically regarded as iterating the sequence of depositing droplets of: (a) a protected monomer onto predetermined locations on a substrate to link with either a suitably activated substrate surface (or with a previously deposited deprotected monomer); (b) deprotecting the deposited monomer so that it can now react with a subsequently deposited protected monomer; and (c) depositing another protected monomer for linking. Different monomers may be deposited at different regions on the substrate during any one cycle so that the different regions of the completed array will carry the different biopolymer sequences as desired in the completed array. One or more intermediate further steps may be required in each iteration, such as oxidation and washing steps.

It is important in such arrays that features actually be present, that they are put down accurately in the desired pattern, are of the correct size, and that the DNA is uniformly coated within the feature. However, in the conventional in situ methods for polynucleotide arrays, phosphoramidite nucleoside monomers are used. In order for the phosphoramidite group to link to a hydroxyl of a previously deposited deprotected polynucleotide monomer, it must first be activated usually by using a weak acid such as tetrazole. However, an activated phosphoramidite is highly reactive with moisture in the air. This leads to a reduction in deposited monomer available for reaction. Furthermore, since water tends to be adsorbed initially at the surface of a droplet which is being used in one cycle of forming a polynucleotide at a feature, the phosphoramidite concentration at the surface of the droplet will tend to be lowest. Consequently, the concentration of a completed probe polynucleotide at a feature of the array, tends to decrease from the center of a feature toward its perimeter. This leads to a decrease in the total signal that should be available when a target to which that polynucleotide hybridizes, is detected. Furthermore, since water vapor concentration the ambient atmosphere may vary, such signal may also vary from array to array, leading to inconsistency in absolute signal generated from different arrays of a batch when the same concentration of a target is encountered. The foregoing problems particularly exist where the phosphoramidite is mixed with activator and the mixture deposited as a droplet on the substrate, such as described in PCT publication WO98-41531. The foregoing reference also states that the activator can be deposited onto a previously deposited droplet containing the phosphoramidite. However, the potential for the activated phorphoramidite to react with moisture in the ambient atmosphere still exists. Furthermore, when one droplet is deposited on the other, there is no guarantee of efficient mixing such that the activated phosphoramidite will be evenly present at the substrate surface.

It would be desirable then, in the fabrication of arrays of biopolymers using biomonomers with a linking group which must be activated (such as a phosphoramidite), to provide a means by which potential reactivity of the activated biomonomer with an ambient atmosphere component (such as water vapor in air) can be kept low.

SUMMARY OF THE INVENTION

All The present invention then, provides a method of fabricating an addressable array of biopolymers on a substrate using a biomonomer with a first linking group which must be activated for linking to a substrate bound moiety. The method includes forming on a region of the substrate carrying the substrate bound moiety, a solid activator composition. A biomonomer containing fluid composition is deposited on the region so that the solid activator activates the first linking group and the biomonomer links to the substrate bound moiety. Typically, the foregoing steps are repeated, with a biomonomer deposited and linked to the substrate bound moiety in one cycle acting as the substrate bound moiety for the next cycle, so as to form the biopolymer. However, it will be appreciated that one or more such cycles can be performed.

In the fabrication of a typical array with multiple features, all of the foregoing steps are repeated at each of multiple different regions on the same substrate, where it is desired to form the features. Generally, the biomonomer containing fluid will be deposited after forming the solid activator composition on the region or regions. As to of forming the solid activator composition at the region, one way of accomplishing this is to deposit a composition of solid activator as a fluid composition, and allowing fluid to evaporate. In this case, the fluid composition may have less than 20% by weight of solid activator content, for example 3% to 20% by weight (or even less than 10% by weight). In one aspect of the method, a sufficient amount of the biomonomer fluid composition may be deposited at a region so as to cover an area greater than that covered by the solid activator composition at the same region (or greater than the area covered by the activator fluid composition at the same region, when the solid activator is deposited as a fluid composition).

The biopolymers may in particular be polynucleotides (for example, DNA), in which case the biomonomer is a nucleoside monomeric unit. The activated biomonomer may particularly react with a component in ambient atmosphere. For example, where the biomonomer is a phosphoramidite, it is reactive with water vapor in air. The same or different biomonomers can be deposited at the same region in different cycles. Furthermore, the same or different fluids can be used for the biomonomer fluid and activator fluid compositions. In one particular case, the fluid of the solid activator fluid composition may have a boiling point of less than 100° C. (or less than 90° C. or even less than 85° C.) while the fluid of the biomonomer containing fluid composition has a boiling point of greater than 100° C. (or greater than 105° C. or even greater than 110° C.).

In a particular aspect of the above array fabrication methods of the present invention, a deposition system is used which has a head with multiple pulse jets each of which can dispense fluid droplets onto the substrate. Each such jet includes a chamber with an orifice, and an ejector which, when activated, causes a droplet to be ejected from the orifice. Such deposition apparatus can be used to dispense droplets of the biomonomer containing fluid and, optionally, to also dispense droplets of the solid activator fluid composition. Alternatively, it will be appreciated that in methods of the present invention for fabricating arrays, the fluid composition of solid activator could be applied as a continuous layer over multiple regions.

The present invention also provides a method of evaluating for the presence of a target polynucleotide in a sample, using an addressable array fabricated in accordance with any of the methods of the present invention. The evaluation method comprises exposing the sample to the array, such that target polynucleotide which may be present will bind to one or more predetermined regions of the array. Optionally, a binding pattern on the array may then be observed and the presence of the target polynucleotide evaluated based on the observed binding pattern. However, this can be done either within a short time following the foregoing steps, or potentially at some indefinite later time.

The present invention further provides an apparatus for fabricating an addressable array of biopolymers on a substrate according to a target pattern. The apparatus includes a deposition system which can separately dispense onto a substrate, fluid compositions of different biomonomers each with a first linking group which must be activated for linking to a substrate bound moiety, and a fluid composition of a solid activator. The apparatus further includes a processor to operate the deposition system. The processor derives from the target array pattern a target drive pattern for operating the deposition system to form the array. The target drive pattern includes instructions to the deposition system to deposit the fluid composition of solid activator at each region at which a biomonomer is to be deposited, separate from and preceding deposition of the biomonomer. The deposition system can include one or multiple pulse jets which can dispense droplets of the different biomonomer fluid compositions, and at least one pulse jet which can separately dispense the activator fluid composition. Each jet includes a chamber with an orifice, and an ejector which, when activated, causes a droplet to be ejected from the orifice. Optionally, the target drive pattern may include ejector instructions such that a droplet of biomonomer fluid composition deposited at a region will cover an area greater than that covered by a preceding droplet of activator fluid composition at the same region.

A still further aspect of the present invention includes a computer program product, for use on an apparatus (such as an apparatus of the above described type) for fabricating an addressable array of biopolymer probes on a substrate according to a target array pattern. The program product includes a computer readable storage medium having a computer program stored thereon. The program, when loaded into a computer of the apparatus derives from the target array pattern a target drive pattern for operating a deposition system of the apparatus to form the array. This target drive pattern includes instructions to the deposition system to deposit the fluid composition of solid activator at each region at which a biomonomer monomer is to be deposited, separate from and preceding deposition of the biomonomer. Optionally, the target drive pattern may include instructions to the deposition system to deposit sufficient biomonomer fluid composition at a region which will cover an area greater than that covered by a preceding droplet of activator fluid composition at the same region.

While the substrates referenced in the aspects of the apparatus, methods and programs of the present invention described above, carry biopolymers, the present invention contemplates that these particular moieties can readily be replaced with other moieties (such as other chemical or biochemical moieties, for example various small molecules) in any of the apparatus, methods or kits of the present invention, where activation of a component is required and particularly where the activated component is more reactive with a component of the ambient atmosphere than is the unactivated component. Thus, wherever a reference is made to biopolymers, this can be replaced with a reference to any such moieties.

The present invention then, including methods, apparatus, and computer program products thereof, can provide any one or more, of a number of useful benefits. For example, in the fabrication of arrays of biopolymers using biomonomers with a linking group which must be activated (such as a phosphoramidite), the present invention provides a means by which potential reactivity of the activated biomonomer with an ambient atmosphere component can be kept low.

BRIEF DESCRIPTION OF THE DRAWINGS

FIG. 1 is a perspective view of a substrate bearing multiple arrays, as may be produced by a method and apparatus of the present invention;

FIG. 2 is an enlarged view of a portion of FIG. 1 showing some of the identifiable individual regions (or "features") of a single array of FIG. 1;

FIG. 3 is an enlarged cross-section of a portion of FIG. 2;

To facilitate understanding, identical reference numerals have been used, where practical, to designate identical elements that are common to the figures.

DETAILED DESCRIPTION OF EMBODIMENTS OF THE INVENTION

Figure 4:
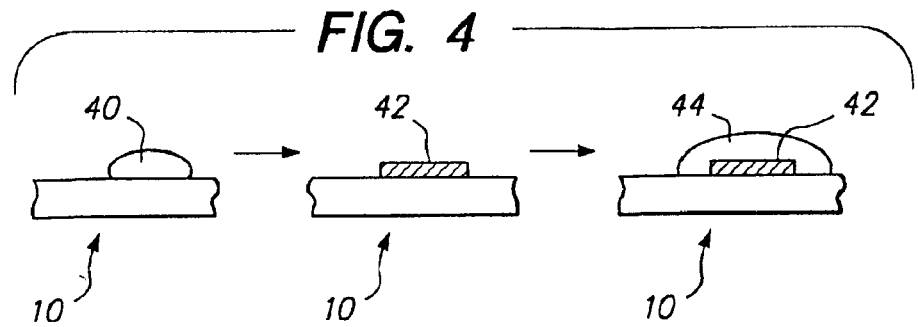
FIG. 4 is an enlarged cross-section illustrating a sequence of events in a method of the present invention during formation of one feature of an array.

In the present application, unless a contrary intention appears, the following terms refer to the indicated characteristics. A "biopolymer" is a polymer of one or more types s of repeating units. Biopolymers are found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. A "nucleotide" refers to a subunit of a nucleic acid and has a phosphate group, a 5 carbon sugar and a nitrogen containing base, as well as analogs of such subunits. A "nucleoside" is of the same structure but without a phosphate group. Specifically, a "biopolymer" includes DNA (including cDNA), RNA and oligonucleotides. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution). A "phosphoramidite" includes a group of the structure of formula (I) below:

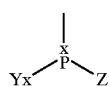

(I)

wherein either X is a linking atom such as O or S and may be the same or different; Y is a protecting group such as cyanoethyl; Z may be a halogen (particularly Cl or Br) or a secondary amino group such as morpholino or N(lower alkyl)$_2$ where the alkyl groups are the same or different, preferably N(i-propyl)$_2$. By "lower alkyl" is referenced 1 to 8 C atoms. A nucleoside phosphoramidite has a nucleoside or a nucleoside analog with the sugar ring bonded to the free bond on the X in formula (I). For example, one particular nucleoside phosphoramidite is represented by formula (II) below:

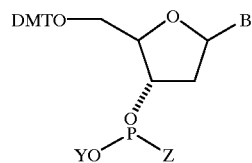

(II)

wherein B is a nucleoside base, and DMT is dimethoxytrityl. The O (which may instead be replaced by S) to which DMT is bonded, acts as a second linking group which is protected by the DMT. Protecting groups other than DMT may be used, and their removal during deprotection is known in oligonucleotide synthesis. Other nucleoside phosphoramidites are also known, for example ones in which the phosphoramidite group is bonded to a different location on the 5-membered sugar ring. Phosphoramidites and nucleoside phosphoramidites are described in U.S. Pat. Nos. 5,902,878, 5,700,919, 4,415,732, PCT publication WO 98/41531 and the references cited therein, among others. A "group" includes both substituted and unsubstituted forms. An "addressable array" includes any one or two dimensional arrangement of discrete regions (or "features") bearing particular biopolymer moieties (for example, different polynucleotide sequences) associated with that region and positioned at if particular predetermined locations on the substrate (each such location being an "address"). These regions may or may not be separated by intervening spaces. It will also be appreciated that throughout the present application, words such as "upper", "lower" and the like are used with reference to a particular orientation of the apparatus with respect to gravity, but it will be understood that other operating orientations of the apparatus or any of its components, with respect to gravity, are possible. Reference to a "droplet" being dispensed from a pulse jet herein, merely refers to a discrete small quantity of fluid (usually less than about 1000 pL) being dispensed upon a single pulse of the pulse jet (corresponding to a single activation of an ejector) and does not require any particular shape of this discrete quantity. When a "spot" is referred to, this may reference a dried spot on the substrate resulting from drying of a dispensed droplet, or a wet spot on the substrate resulting from a dispensed droplet which has not yet dried, depending upon the context. "Fluid" is used herein to reference a liquid. Use of the singular in reference to an item, includes the possibility that there may be multiple numbers of that item. A "solid" may still have some amount of a carrier fluid, such as a solvent, present. However, typically a "solid" will have no more than 20% by weight (and often less than 10% or 5%, or 1%, by weight, of such carrier fluid present). A "solid activator" is one which is solid at the operating temperature at which it is used (normally at around a typical room temperatures, such as between 10° C. to 30° C.). By one item being "remote" from another is referenced that they are at least in different buildings, and may be at least one, at least ten, or at least one hundred miles apart.

Referring first to FIGS. 1–3, typically the present invention will produce multiple identical arrays 12 (only some of which are shown in FIG. 1) across a complete front surface 11a of a single substrate 10 (which also has a back surface 11b). However, the arrays 12 produced on a given substrate need not be identical and some or all could be different. Each array 12 will contain multiple spots or features 16. The arrays 12 are shown as being separated by spaces 13. A typical array 12 may contain from 100 to 100,000 features. All of the features 16 may be different, or some or all could be the same. Each feature carries a predetermined polynucleotide having a particular sequence, or a predetermined mixture of polynucleotides. This is illustrated schematically in FIG. 3 where different regions 16 are shown as carrying different polynucleotide sequences. While arrays 12 are shown separated from one another by spaces 13, and the features 16 are separated from one another by spaces, such spaces in either instance are not essential.

Figure 5:
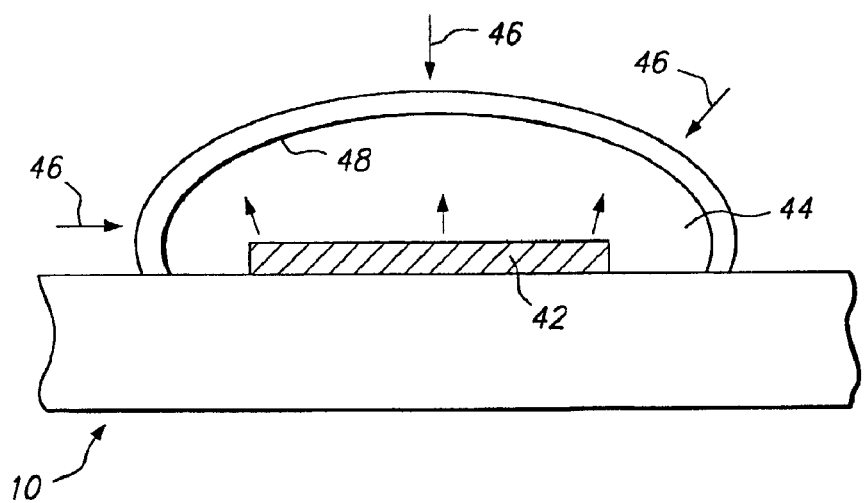
FIG. 5 is an enlarged view of a portion of FIG. 4.

Referring to FIGS. 4 and 5 in particular, the principle of the present invention can be understood. These FIGS. are not to scale, with some features being exaggerated for clarity. It will be assumed that a substrate bound moiety is present at least at the location of each feature or region to be formed. Such substrate bound moiety may, for example, be a nucleoside monomer has been deposited and deprotected at the location of each feature, such that the second linking group is available for linking to another activated nucleoside monomer. Alternatively, the substrate bound moiety may be a suitable linking group previously attached to substrate 10. Both of these steps are known in in situ fabrication techniques. FIGS. 4 and 5 illustrate only one region of an array being fabricated. A droplet 40 of a solution of a solid activator is deposited onto the region carrying the substrate bound moiety. The solvent of the solution is allowed to evaporate to form a layer 42 of solid activator on substrate 10. Given the volume of a typical droplet, and the solvents which may be used, as discussed herein, this evaporation will typically take place in less than one second (and may be completed in less than 0.5 or even 0.25 seconds). A droplet 44 of a biomonomer solution, such as a nucleoside phosphoramidite monomer, is then deposited onto the region. Preferably, but not necessarily, this droplet 44 will cover an area which is greater than that covered by the droplet 40 and hence greater than the area covered by layer 42. As a result of the above steps, solid activator of layer 42 will activate the first linking group of the biomonomer, specifically the phosphoramidite group of a nucleoside monomer, such that the activated group will then link with the substrate bound moiety (again, a linking group previously attached to substrate 10 or a deprotected nucleoside monomer deposited in a previous cycle).

The above steps can be repeated at the illustrated region in FIGS. 4 and 5, until the desired biopolymer has been synthesized. It will be understood however, that intermediate oxidation, deprotection, washing and other steps may be required between cycles, as is well known in the art of synthesizing biopolymers (such as oligonucleotides). These cycles may be repeated using different or the same biomonomers, at multiple regions over multiple cycles, as required to fabricate the desired array or arrays 12 on substrate 10.

As discussed above, the activated biomonomer (such as the activated phosphoramidite) may be reactive with a component in the ambient atmosphere (such as water vapor). However, as best seen in FIG. 5, activated biomonomer is generated adjacent the layer 42 of solid activator. Even if the ambient atmosphere component of concern may dissolve in droplet 44 to some extent, possibly even forming a frontal boundary 48 therein, it will be appreciated that activated monomer near layer 42 will not be exposed to that component for some time, if at all. This will allow time for the activated monomer to link to the surface bound moiety.

Figure 6:
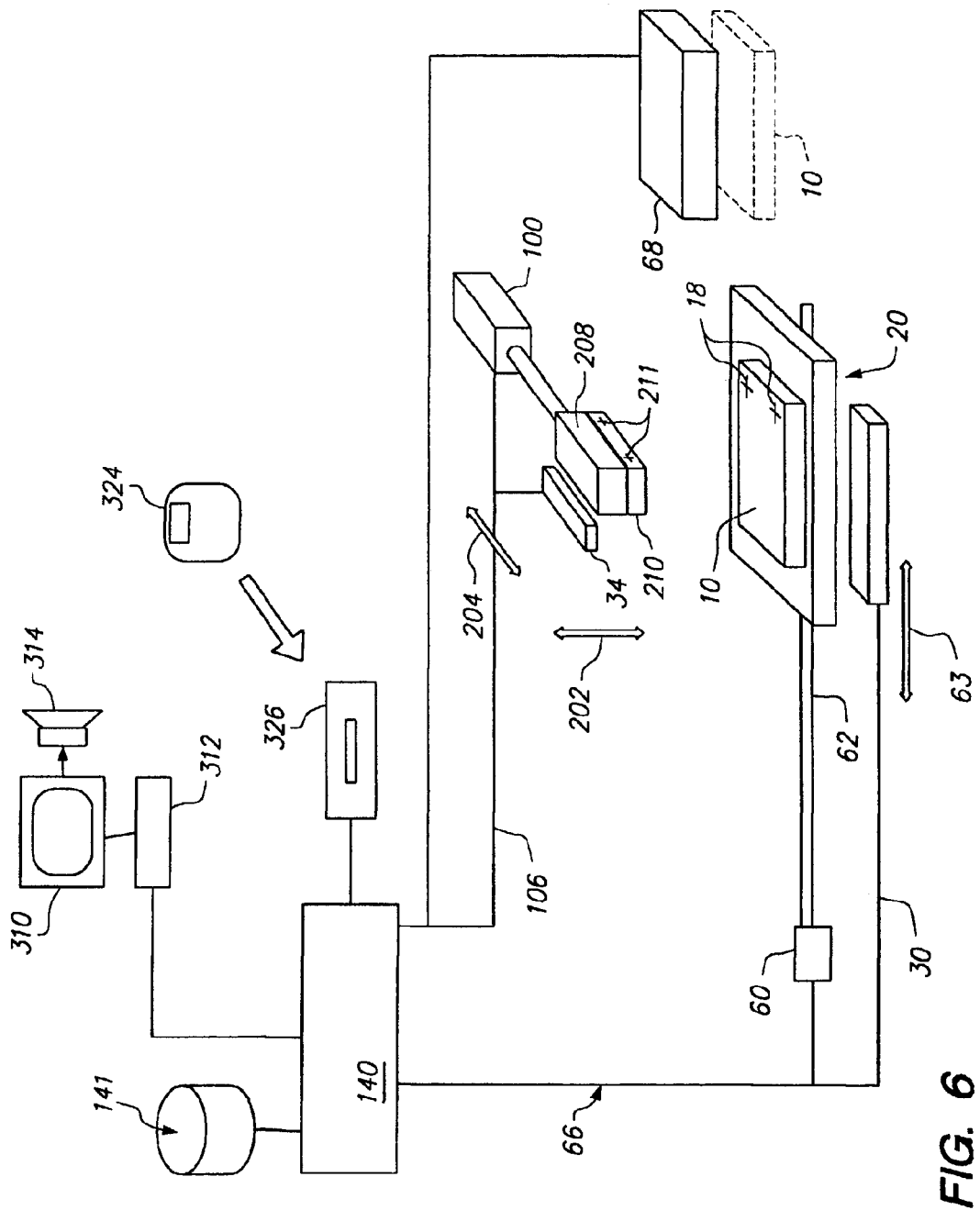
FIG. 6 is a schematic view of apparatus of the present invention.

Referring now to FIG. 6 the apparatus shown includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 14 without exerting too much pressure thereon, since substrate 14 is often made of glass. A flood station 68 is provided which can expose the entire surface of substrate 10, when position beneath station 68 as illustrated in broken lines in FIG. 4, to a fluid typically used in the in situ process, and to which all features must be exposed during each cycle (for example, oxidizer, deprotection agent, and wash buffer).

A dispensing head 210 is retained by a head retainer 208. The positioning system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head 210, by moving it in the direction of arrow 63, while transporter 100 is used to provide adjustment of the position of head retainer 208 (and hence head 210) in a direction of axis 204. In this manner, head 210 can be scanned line by line, by scanning along a line over substrate 10 in the direction of axis 204 using transporter 100, while line by line movement of substrate 10 in a direction of axis 63 is provided by transporter 60. Transporter 60 can also move substrate holder 20 to position substrate 10 beneath flood station 68 (as illustrated in broken lines in FIG. 4). Head 210 may also optionally be moved in a vertical direction 202, by another suitable transporter (not shown). It will be appreciated that other scanning configurations could be used. It will also be appreciated that both transporters 60 and 100, or either one of them, with suitable construction, could be used to perform the foregoing scanning of head 210 with respect to substrate 10. Thus, when the present application recites "positioning" one element (such as head 210) in relation to another element (such as one of the stations 20 or substrate 10) it will be understood that any required moving can be accomplished by moving either element or a combination of both of them. The head 210, the positioning system, and processor 140 together act as the deposition system of the apparatus. An encoder 30 communicates with processor 140 to provide data on the exact location of substrate station 20 (and hence substrate 10 if positioned correctly on substrate station 20), while encoder 34 provides data on the exact location of holder 208 (and hence head 210 if positioned correctly on holder 208). Any suitable encoder, such as an optical encoder, may be used which provides data on linear position.

Head 210 may be of a type commonly used in an ink jet type of printer and may, for example, include five or more chambers (at least one for each of four nucleoside phosphoramidite monomers plus at least one for a solution of solid activator) each communicating with a corresponding set of multiple drop dispensing orifices and multiple ejectors which are positioned in the chambers opposite respective orifices. Each ejector is in the form of an electrical resistor operating as a heating element under control of processor 140 (although piezoelectric elements could be used instead). Each orifice with its associated ejector and portion of the chamber, defines a corresponding pulse jet. It will be appreciated that head 210 could, for example, have more or less pulse jets as desired (for example, at least ten or at least one hundred pulse jets). Application of a single electric pulse to an ejector will cause a droplet to be dispensed from a corresponding orifice. Certain elements of the head 210 can be adapted from parts of a commercially available thermal inkjet print head device available from Hewlett-Packard Co. as part no. HP51645A. Alternatively, multiple heads could be used instead of a single head 210, each being similar in construction to head 210 and being provided with respective transporters under control of processor 140 for independent movement. In this alternate configuration, each head may dispense a corresponding biomonomer (for example, one of four nucleoside phosphoramidites) or a solution of a solid activator.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The apparatus can deposit droplets to provide features which may have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

The apparatus further includes a display 310, speaker 314, and operator input device 312. Operator input device 312 may, for example, be a keyboard, mouse, or the like. Processor 140 has access to a memory 141, and controls print head 210 (specifically, the activation of the ejectors therein), operation of the positioning system, operation of each jet in print head 210, and operation display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the steps required by the present invention, or any hardware or software combination which will perform those or equivalent steps. The programming can be provided remotely to processor 141, or previously saved in a computer program product such as memory 141 or some other portable or fixed computer readable storage medium using any of those devices mentioned below in connection with memory 141. For example, a magnetic or optical disk 324 may carry the programming, and can be read by disk reader 326.

Operation of the apparatus of FIG. 4 in accordance with a method of the present invention, will now be described with reference to FIG. 6 in particular. First, it will be assumed that memory 141 holds a target drive pattern. This target drive pattern is the instructions for driving the apparatus components as required to form the target array (which includes target locations and dimension for each spot) on substrate 10 and includes, for example, movement commands to transporters 60 and 100 as well as firing commands for each of the pulse jets in head 210 coordinated with the movement of head 210 and substrate 10. This target drive pattern is based upon the target array pattern and can have either been input from an appropriate source (such as input device 312, a portable magnetic or optical medium, or from a remote server, any of which communicate with processor 140), or may have been determined by processor 140 based upon an input target array pattern (using any of the appropriate sources previously mentioned) and the previously known nominal operating parameters of the apparatus. The target drive pattern further includes instructions to head 210 and the positioning system of the apparatus to deposit the solution of solid activator at each region at which a biomonomer is to be deposited, separate from and preceding deposition of the biomonomer. Further, it will be assumed that each of four chambers of head 210 has been loaded with four different nucleoside phosphoramidite monomers, while a fifth chamber has been loaded with activating agent. It will also be assumed that flood station 68 has been loaded with all necessary solutions. Operation of the following sequences are controlled by processor 140, following initial operator activation, unless a contrary indication appears.

Figure 7:
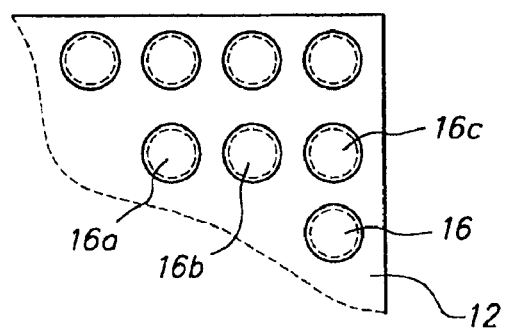
FIG. 7 is a view similar to that of FIG. 2 but illustrating a preferred method in which the area occupied by biomonomer solution at a region during any one cycle, is greater than that covered by a deposited solid activator layer previously deposited in the same cycle.

For any given substrate 10, the operation is basically as follows, assuming in situ preparation of a typical oligonucleotide using standard nucleoside phosphoramidite monomers as the biomonomers. A substrate 10 is loaded onto substrate station 20 either manually by an operator, or optionally by a suitable automated driver (not shown) controlled, for example, by processor 140. A target drive pattern necessary to obtain a target array pattern, is determined by processor 140 (if not already provided), based on nominal operating parameters of the apparatus. The apparatus is then operated as follows: (a) if not the first cycle, position substrate 10 at flood station 68 and for all regions of the arrays being formed, deprotected previously deposited and linked biomonomer on substrate 10 at flood station 68; (b) move substrate 10 to receive droplets from head 210 and deposit droplets of solution of solid activator from one or more pulse jets of head 210 onto each region in accordance with to the target drive pattern for each of multiple arrays 12; (c) allow sufficient time for activator solution to evaporate leaving layer 42 of solid activator; (c) dispense appropriate next biomonomer onto each region such that the first linking group is activated by solid activator and links to previously deposited deprotected biomonomer; (d) move substrate 10 back to flood station 68 for oxidation, capping, and washing steps over entire substrate as required; and (e) repeat foregoing cycle for all the regions of all desired arrays 12 until the desired arrays are completed (note that the biomonomer deposited and linked to the substrate bound moiety in one cycle becomes the substrate bound moiety for the next cycle). During each cycle, the relative areas covered by the solid activator and a biopolymer solution deposited immediately following formation of the solid activator, are illustrated in FIG. 7 which is a view similar to that of FIG. 2. In FIG. 7, for each region the area occupied by a droplet of a biomonomer solution is indicated by a solid line circle, while the lesser area occupied by a layer 42 of solid activator formed from a droplet deposited immediately preceding the droplet of biomonomer solution, is illustrated by a broken line circle. Note that the area of the final features will be equal to that of the broken line circles.

Note that during the above operation, pressure within head 210 can be controlled as described in co-pending patent applications "FABRICATING BIOPOLYMER ARRAYS", by Caren et al., Ser. No. 09/302,922, and "PREPARATION OF BIOPOLYMER ARRAYS" by A. Schleifer et al., Ser. No. 09/302,899, both filed Apr. 30, 1999 and both assigned to the same assignee as the present application, and the references cited therein. Those references and all other references cited in the present application, are incorporated into this application by reference. Processor 140 can execute the control of pressure within head 210.

With regard to the actual deposition sequence of biomonomer or activator solution droplets, as already mentioned, in this sequence processor 140 will operate the apparatus according to the target drive pattern, by causing the positioning system to position head 210 facing substrate station 20, and particularly the mounted substrate 10, and with head 210 at an appropriate distance from substrate 10. Processor 140 then causes the positioning system to scan head 210 across substrate 14 line by line (or in some other desired pattern), while coordinating activation of the ejectors in head 210 so as to dispense droplets in accordance with the target pattern. This can be continued until all arrays 12 to be formed on substrate 10 have been completed. The number of spots in any one array 12 can, for example, be at least ten, at least one hundred, at least one thousand, or even at least one hundred thousand.

At this point the droplet dispensing sequence is complete. In an alternative to the above described embodiment, the activator solution can be deposited as a film over the entire substrate 10, rather than being deposited as droplets only at the location of the desired features. This can save time, although activator solution will be wasted since only activator at locations of subsequently deposited biomonomer (the desired feature locations) will be used, and the rest will be washed off.

In the case of phosphoramidites, suitable activators are known and include tetrazole, S-ethyl tetrazole, dicyanoimidazole ("DCI"), or benzimidazolium triflate. As to solvents for the activator, any low boiling point solvent as already mentioned, could be used provided it is otherwise compatible with the chemistry being used. In the case of phosphoramidites a non-protic low boiling point solvent could be used, for example, acetonitrile, dioxane, toluene, ethylacetate, acetone, tetrahydrofuran, and the like. Solvents for the biomonomers are already known, such as those solvents described in PCT publication WO 98/41531 and the references cited therein.

Arrays fabricated by methods and apparatus of the present invention, can be used to evaluate for the presence of one or more target polynucleotides in a known manner. Basically, this involves exposing the sample, normally as a fluid composition, to the array, such that target polynucleotide which may be present will bind to one or more predetermined regions of the array. The binding pattern on the array may then be observed by any method (such as by observing a fluorescence pattern), and the presence of the target evaluated based, in whole or in part, on the observed binding pattern.

Modifications in the particular embodiments described above are, of course, possible. For example, where a pattern of arrays is desired, any of a variety of geometries may be constructed other than the organized rows and columns of arrays 12 of FIG. 1. For example, arrays 12 can be arranged in a series of curvilinear rows across the substrate surface (for example, a series of concentric circles or semi-circles of spots), and the like. Similarly, the pattern of regions 16 may be varied from the organized rows and columns of spots in FIG. 2 to include, for example, a series of curvilinear rows across the substrate surface(for example, a series of concentric circles or semi-circles of spots), and the like. Even irregular arrangements of the arrays or the regions within them can be used, at least when some means is provided such that during their use the locations of regions of particular characteristics can be determined (for example, a map of the regions is provided to the end user with the array).

The present methods and apparatus may be used to deposit biopolymers or other moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12. Substrates of other configurations and equivalent areas can be chosen. The configuration of the array may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; fused silica, silicon, plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated), Various modifications to the embodiments of the particular embodiments described above are, of course, possible. Accordingly, the present invention is not limited to the particular embodiments described in detail above.

What is claimed is:

1. An apparatus for fabricating an addressable array of biopolymers on a substrate according to a target pattern, comprising:
   (a) a deposition system which can separately dispense onto a substrate, fluid compositions of different biomonomers each with a first linking group which must be activated for linking to a substrate bound moiety, and a fluid composition of a solid activator;
   (b) a processor to operate the deposition system, which processor derives from the target array pattern a target drive pattern for operating the deposition system to form the array, the target drive pattern comprising instructions to the deposition system to perform the following at each of multiple regions at which a biomonomer is to be deposited:
      (i) deposit the fluid composition of solid activator separate from and preceding deposition of the biomonomer;
      (ii) allow sufficient time for evaporation to leave solid activator at the region; and
      (iii) then deposit the biomonomer.

2. An apparatus according to claim 1 wherein the deposition system comprises multiple pulse jets which can dispense droplets of the different biomonomer fluid compositions and at least one pulse jet which can separately dispense the activator fluid composition, each jet comprising: a chamber with an orifice; and an ejector which, when activated, causes a droplet to be ejected from the orifice.

3. An apparatus according to claim 1 wherein the processor derives a target drive pattern which repeats (i) to (iii) at each of multiple features.

4. An apparatus according to claim 1 wherein the deposition system comprises a head having multiple pulse jets which can dispense droplets of the different biomonomer fluid compositions.

5. An apparatus for fabricating an addressable array of biopolymers on a substrate according to a target pattern, comprising:
   (a) a deposition system which can separately dispense onto a substrate, fluid compositions of different biomonomers each with a first linking group which must be activated for linking to a substrate bound moiety, and a fluid composition of a solid activator; and
   (b) a processor to operate the deposition system, which processor derives from the target array pattern a target drive pattern for operating the deposition system to form the array, the target drive pattern comprising instructions to the deposition system to deposit the fluid composition of solid activator at each region at which a biomonomer is to be deposited, separate from and preceding deposition of the biomonomer;
   wherein the deposition system comprises multiple pulse jets which can dispense droplets of the different biomonomer fluid compositions and at least one pulse jet which can separately dispense the activator fluid compositions, each jet comprising: a chamber with an orifice; and an ejector which, when activated, causes a droplet to be ejected from the orifice; and
   wherein the target drive pattern comprises ejector instructions such that a droplet of biomonomer fluid composition deposited at a region will cover an area greater than that covered by a preceding droplet of activator fluid composition at the same region.

* * * * *